(12) United States Patent
Roy

(10) Patent No.: US 8,858,924 B2
(45) Date of Patent: Oct. 14, 2014

(54) COMPOSITIONS AND METHODS FOR TREATMENT OF HEMORRHAGE

(75) Inventor: Josee Roy, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 698 days.

(21) Appl. No.: 12/411,548

(22) Filed: Mar. 26, 2009

(65) Prior Publication Data

US 2010/0247676 A1  Sep. 30, 2010

(51) Int. Cl.

| | |
|---|---|
| *A61K 31/765* | (2006.01) |
| *A61K 45/06* | (2006.01) |
| *A61K 31/77* | (2006.01) |
| *A61K 31/74* | (2006.01) |
| *A61K 9/00* | (2006.01) |
| *A61K 47/10* | (2006.01) |
| *A61K 33/06* | (2006.01) |
| *C07C 31/20* | (2006.01) |
| *C07F 3/02* | (2006.01) |

(52) U.S. Cl.
CPC ............... *A61K 31/74* (2013.01); *A61K 45/06* (2013.01); *A61K 31/77* (2013.01); *A61K 33/06* (2013.01); *A61K 9/0019* (2013.01); *A61K 47/10* (2013.01)
USPC .................. 424/78.08; 424/78.18; 424/78.37; 424/681; 424/692; 424/697

(58) Field of Classification Search
USPC ....... 424/78.08, 227, 423, DIG. 13; D24/108, D24/114, 169
See application file for complete search history.

(56) References Cited

U.S. PATENT DOCUMENTS

| | | | |
|---|---|---|---|
| 3,026,248 A | 3/1962 | Noseworthy et al. | |
| 4,020,162 A | 4/1977 | Ghilardi et al. | |
| 4,451,447 A | 5/1984 | Kaplan et al. | |
| 5,605,687 A * | 2/1997 | Lee ............................ | 424/78.06 |
| 7,582,680 B1 | 9/2009 | Shi et al. | |
| 7,837,987 B2 | 11/2010 | Shi et al. | |
| 7,892,721 B2 * | 2/2011 | Cioc et al. ..................... | 430/290 |
| 2003/0118545 A1 | 6/2003 | Shi et al. | |

(Continued)

FOREIGN PATENT DOCUMENTS

| | | |
|---|---|---|
| EP | 0109310 A2 | 5/1984 |
| EP | 1913962 A1 | 4/2008 |

(Continued)

OTHER PUBLICATIONS

Epstein et al., "Time course of hemosiderin production by alveolar macrophages in a murine model," 2001, Chest, 120(6): 2013-2020.*

(Continued)

*Primary Examiner* — Jane C Oswecki
(74) *Attorney, Agent, or Firm* — William D. Schmidt; Sorell, Lenna & Schmidt, LLP

(57) ABSTRACT

Methods of treating hemorrhage are provided, comprising diagnosing one or more hemorrhaging or potentially hemorrhaging vessels in a patient and administering to the patient a therapeutically effective amount of a composition comprising a vessel closing compound at a concentration between about 0.1% and about 45%. The vessel closing compound may comprise a polymer with hydrophilic properties, such as polyethylene glycol (PEG). The composition may also comprise one or more active agent such as a blood flow modifier with a potential to form ionic bonds with the vessel closing agent.

14 Claims, 5 Drawing Sheets

(56) References Cited

U.S. PATENT DOCUMENTS

| | | | |
|---|---|---|---|
| 2004/0214790 | A1 | 10/2004 | Borgens |
| 2005/0069520 | A1 | 3/2005 | Shi et al. |
| 2007/0258938 | A1* | 11/2007 | Roy et al. ............... 424/78.3 |
| 2007/0259044 | A1* | 11/2007 | Roy et al. ............... 424/486 |
| 2008/0050356 | A1 | 2/2008 | Pakola et al. |

FOREIGN PATENT DOCUMENTS

| | | | |
|---|---|---|---|
| GB | 1250304 | A | 10/1971 |
| GB | 1286351 | A | 8/1972 |
| RU | 2173852 | C2 * | 8/1999 |
| WO | WO0128544 | A | 4/2001 |
| WO | WO0277651 | A1 * | 3/2002 ............... C12Q 1/68 |
| WO | 02092107 | | 11/2002 |

OTHER PUBLICATIONS

Shiber et al., Mar. 2010, Am. J. Emerg. Med.; vol. 28, No. 3; pp. 331-333; http://www.ncbi.nlm.nih.gov/pubmed/20223391, downloaded Feb. 16, 2012 (online Abstract only).*

Kameneva et al., 2004, Biorheology; vol. 41; Issue No. 1; pp. 53-64 (Abstract only).*

Shiber et al., Mar. 2010; Am. J. Emerg. Med.; vol. 28, No. 3; pp. 331-333; http://www.ncbi.nih.gov/pubmed/20223391; downloaded Feb. 16, 2012 (online Abstract only—previously supplied).*

Kameneva et al., 2004, Biorheology; 41(1): 53-64 (Abstract only—previously supplied).*

Epstein et al., 2001, Chest, 120(6): 2013-2020 (previously supplied).*

Epstein et al., 2001, Chest, 120(6):2013-2020 (Previously supplied).*

Borgens et al., 2001, J. Neuroscience Research, 66(6):1179-1186.*

Kameneva et al., 2004, Biorheology; 41(1):53-64 (Abstract only—previously supplied).*

Epstein et al., 2001, Chest; 120(6):2013-2020 (Previously supplied).*

Borgens et al., 2001, J. Neuroscience Research, 66(6):1179-1186 (on Form 1449 submitted by Applicant).*

Simpson et al., "Intrathecal magnesium sulfate protects the spinal cord from ischemic injury during thoracic aortic cross-clamping,"; Anesthesiology (1994) vol. 81, pp. 1493-1499.

Lang-Lazdunski et al., "Prevention of ischemic spinal cord injury: comparative effects of magnesium sulfate and riluzole,"Journal of Vascular Surgery (Jul. 2000); vol. 32; No. 1; pp. 179-189.

Ancill, R.J., "The blood volume of the normal guinea-pig," J. Physiol. (1956)132, pp. 469-475.

Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.

Borgens R B and Bohnert D., "Rapid recovery from spinal cord injury after subcutaneously administered polyetheylene glycol," Journal of Neuroscience Research (2001); vol. 66, pp. 1179-1186.

Ditor D S et al., "Effects of polyethylene glycol and magnesium sulfate administration on cinically relevant neurological outcomes after spinal cord injury in the rat," Journal of Neuroscience Research (2007); vol. 85, pp. 1458-1467.

The International Search Report and The Written Opinion of the International Searching Authority in PCT/US2007/067580, (Dec. 28, 2010).

Turner, et al., "Magnesium gluconate offers no more protection than magnesium sulphate following diffuse traumatic brain injury in rats.", Journal of the American College of Nutrition. 23(51 (2004), 541S-544S.

Muir, et al., "Magnesium for acute stroke (Intravenous Magnesium Efficacy in Stroke trial): randomised controlled trial.". The Lancet, 363(9407). (Feb. 7, 2004). 439-45.

Saver, et al., "Prehospital Neuroprotective Therapy for Acute Stroke: Results of the Field Administration of Stroke Therapy-Magnesium (FAST-MAG) Pilot Trial.", Stroke, 35(5). (2004). 106-108.

Bittner, et al., "Reconnection of severed nerve axons with polyethylene glvcol.". Brain Research, 367(1-2), (1986), 351-355.

McIntosh, et al., "Magnesium protects against neurological deficit after brain injury.". Brain Research. 482(2). (1989). 252-260.

Shapiro, et al., "Oscillating field stimulation for complete spinal cord injury in humans: a Phase 1 trial.", J. Neurosurg Spine, 2(1), (Jan. 2005), 3-10.

Resende, et al., Local transcutaneous electrical stimulation (TENS) effects in experimental inflammatory edema and pain, European Journal of Pharmacology 504(1) (2004), 217-222.

Kwon, et al. "Magnesium Chloride in a Polyethylene Glycol Formulation as a Neuroprotective Therapy for Acute Spinal Cord Injury: Preclinical Refinement and Optimization," Journal of Neurotrauma 26, 1379-1393 (Aug. 2009).

Kwon, et al. "A Grading System to Evaluate Objectively the Strength of Pre-Clinical Data of Acute Neuroprotective Therapies for Clinical Translation in Spinal Cord Injury," Journal of Neurotrauma, 28, 1525-1543 (Aug. 2011).

Kwon, et al. "Translational Research in Spinal Cord Injury: A Survey of Opinion from the SCI Community," Journal of Neurotrauma, 27, pp. 21-33 (Jan. 2010).

McKee, et al. "Analysis of the Brain Bioavailability of Peripherally Administered Magnesium Sulfate: A Study in Humans with Acute Brain Injury Undergoing Prolonged Induced Hypermagnesemia," Crit. Care Med., 33(3), 661-666 (Mar. 2005).

Journal of Spinal Cord Medicine, 34(6), 620-621 (2011).

W.M. van den Bergh, et al. "Magnesium therapy after aneurysmal subarachnoid haemorrhage a dose-finding study for long term treatment," Acta Neurochir (2003) 145: 195-199.

W.M. Van Den Bergh, et al., Magnesium therapy after aneurysmal subarachnoid haemorrhage a dose-finding study for long term treatment. Acta Neurochir. 2003, vol. 145, pp. 195-199.

International Search Report and Written Opinion for US Application PCT/US2010/028228 mailed on Dec. 10, 2010.

* cited by examiner

Accumulation and retention of biotin-labeled PEG within the hemorrhage site over a period of one week following administration of a magnesium in biotin-PEG formulation Fig. 1a
Fig. 1b
Fig. 1c
Fig. 1d
Fig. 1e
Fig. 1f Accumulation of biotin-labeled PEG within the hemorrhage site following different modes of administration of a biotin-PEG solution Fig. 2a   Fig. 2b   Fig. 2c
Fig. 2d   Fig. 2e   Fig. 2f

COMPOSITIONS AND METHODS FOR TREATMENT OF HEMORRHAGE

FIELD OF THE INVENTION

This invention relates to methods and compositions for treatment of hemorrhage.

BACKGROUND OF THE INVENTION

Bleeding, technically known as hemorrhage or hemorrhaging, is the loss of blood from the circulatory system. Bleeding can occur either internally, where blood leaks from blood vessels inside the body, or externally, where blood leaks through a natural opening or through a break in the skin. Bleeding occurs when a blood vessel within the body is ruptured or leaks. It can result from physical trauma or non-traumatic causes such as a ruptured aneurysm. Anticoagulant therapy, as well as disorders with blood clotting can heighten the risk that a hemorrhage will occur. A ruptured aneurysm can cause severe internal bleeding which can lead to shock or even death. The current treatment options are surgery to repair the aneurysm (if possible), bed rest and medications (such as painkillers and anti-seizure drugs) to ease associated symptoms. Around one-half of all people who experience a ruptured aneurysm die either within the first day or the next three months. About fifty percent (50%) of the survivors are usually left with lifelong disabilities.

Accordingly, there is a need in the art for a method to control bleeding and reduce the risk of deleterious consequences.

SUMMARY OF THE INVENTION

Methods of treating hemorrhage are provided, comprising diagnosing one or more hemorrhaging in a patient and administering to the patient a therapeutically effective amount of a composition comprising a vessel closing compound at a concentration between about 0.1 and about 45% weigh per volume. In compositions for local administration, the concentration of the vessel closing compound is can be between about 0.1% and about 20% weight to volume, and may be between about 1 to 10% weight per volume. For parenteral administration, the concentration can be between about 10% and about 45% weight per volume, and in some embodiments can be between about 20 to about 40% weight to volume. The vessel closing compound may comprise a polymer with hydrophilic properties, such as polyethylene glycol (PEG).

In addition to the vessel closing compound, the composition may include one or more active agents capable of modifying blood flow. In some embodiments, the active agent comprises a magnesium salt (Mg) present at a concentration between about 0.1 and about 20% weight per volume. In some embodiments, the active agent comprises a magnesium salt (Mg) present at a concentration between about 0.1 and about 10% weight per volume. In some embodiments, the active agent comprises a magnesium salt (Mg) present at a concentration between about 0.5 and about 5% weight per volume.

The therapeutically effective amount can be calculated based on the weight of the patient. Generally, the therapeutically effective amount of instant composition to be administered may be estimated based on patient's weight using the ratio of about 0.05 ml to 20 ml of composition per 1 kg of patient's weight. If bleeding persists, a repeat dose may be administered. When administered locally, a lower dose is required with a range of about 0.05 to about 5 ml of composition per kg of patient's weight, about 0.1 to about 5 ml of composition per kg of patient's weight or about 0.1 to about 1 ml of composition per kg of patient's weight. When administered parenterally, a higher dose may be required, with a range of about 0.5 to about 20 ml of composition per kg of patient's weight, about 0.5 to about 10 ml of composition per kg of patient's weight or about 1 to about 8 ml composition per kg of patient's weight. The at least one therapeutically effective amount of the instant composition can be administered within one half-life or less of the vessel closing compound.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIGS. 1a-1f demonstrate accumulation and retention of biotin-labeled PEG within the hemorrhagic site over a period of one week when administered at the time of injury.

FIGS. 2a-2f demonstrate accumulation of biotin-labeled PEG within the hemorrhagic site following different modes of administration at the time of injury.

Figure 3A:
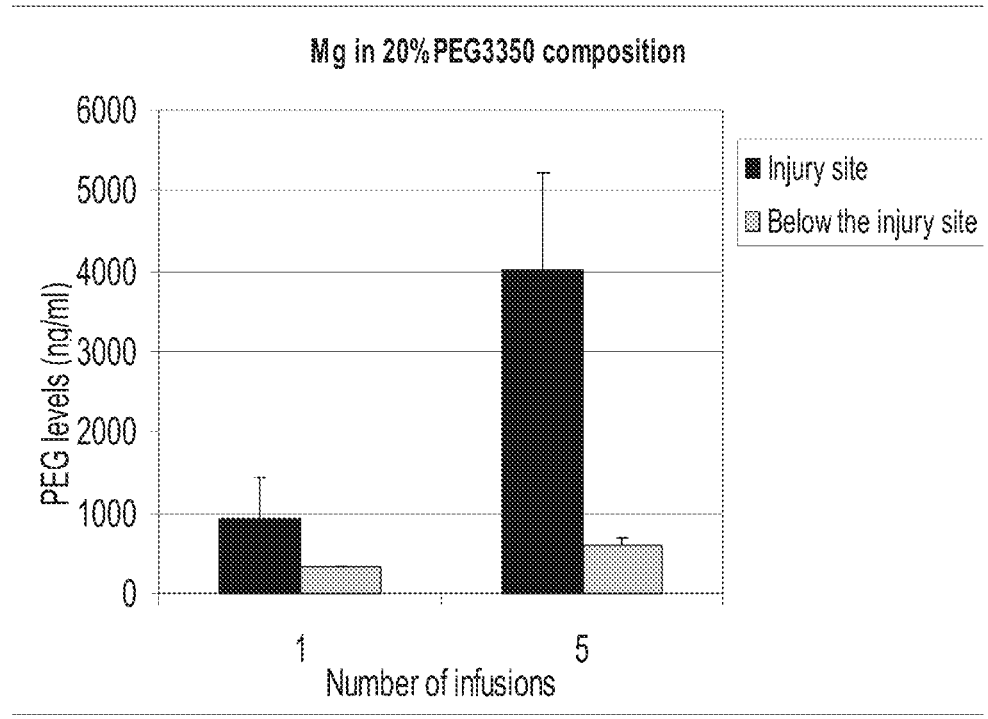
FIGS. 3a and 3b present data of accumulation of PEG within the hemorrhagic site following administration of various PEG compositions.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION OF THE INVENTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent.

Methods of treating hemorrhage are provided. Such methods comprise diagnosing one or more hemorrhaging vessels in a patient and administering to the patient a therapeutically effective amount of a composition comprising a vessel closing compound.

The term "treating" or "treatment" refers to executing a protocol, which may include administering one or more drugs to a patient (human or otherwise), in an effort to alleviate signs or symptoms of the disease. "Treating" or "treatment" does not require complete alleviation of signs or symptoms, does not require a cure, and specifically includes protocols which have only a marginal effect on the patient.

The term "therapeutically effective amount" means a quantity of the instant composition which, when administered to a patient, is sufficient to result in an improvement in patient's condition. The improvement does not mean a cure and may include only a marginal change in patient's condition. It also includes an amount of the active agent that prevents the condition or stops or delays its progression.

The therapeutically effective amount can be calculated based on the weight of the patient. Generally, the therapeutically effective amount of instant composition to be administered may be estimated based on patient's weight using the ratio of about 0.05 ml to 20 ml of composition per 1 kg of patient's weight. If bleeding persists, a repeat dose may be administered. When administered locally, a lower dose is required with a range of about 0.05 to about 5 ml of composition per kg of patient's weight, about 0.1 to about 5 ml of composition per kg of patient's weight or about 0.1 to about 1 ml of composition per kg of patient's weight. When administered parenterally, a higher dose may be required, with a range of about 0.5 to about 20 ml of composition per kg of patient's weight, about 0.5 and about 10 ml of composition per kg of patient's weight or about 1 to about 8 ml composition per kg of patient's weight.

The hemorrhaging may be induced by a mechanical, an electrical, a biological, or a chemical injury. The hemorrhaging may also derive from a degenerative condition such as formation of aneurysm. Any diagnosing method known and used in the art may be utilized to identify existence of one or more hemorrhaging vessels. Vessels that may be at risk of hemorrhaging may also be identified by looking for risk factors, such as aneurysm, abdominal trauma, soft tissue, tendon, ligament or bone trauma, or tumors. Suitable diagnosing methods include, but are not limited to, blood tests, blood pressure tests, EKG, or medical imaging tests, such as X-ray, ultrasound, CAT scans or MRI.

Compounds useful for use as vessel closing compounds in instant compositions may meet the following criteria: 1) they possess hydrophilic properties; 2) they accumulate at the site of hemorrhage and have vessel sealing properties; and 3) they remain at the site of hemorrhage for a period of at least 1 hour, and more preferably at least 24 hours. In addition, for parenteral administration, suitable vessel closing compounds are capable of being rapidly excreted when the blood vessels are intact.

In addition, vessel closing agents may have the ability to seal or fuse cellular membranes under certain conditions. For the instant composition, the concentration of the vessel closing compound may be selected so the vessel closing compound causes membrane sealing effect without a major membrane fusion effect. For example, polyethylene glycols (PEGs) having a molecular weight between 3350 and 8000 DA show significant cell membrane sealing and reduction of hemorrhage at concentrations between 0.1 to 30% weight per volume and significant membrane fusion properties at a concentration of higher than 45% weight per volume. Accordingly, in the some embodiments, the concentration of the vessel closing compound is less than 45% weight per volume.

For this application, various compositions will comprise vessel closing compounds that are retained at the hemorrhagic site but may be rapidly excreted from the systemic circulation if the vessels are intact. The rate of systemic clearance, or half-life, of vessel closing compounds is related to the molecular weight and the hydrophilic properties of the compound. In general, for the same molecular weight, hydrophilic polymers have shorter half-lives than more hydrophobic polymers. Furthermore, the half-lives of polymers with hydrophilic properties are directly linked to their molecular weight with higher molecular weight polymers having longer half-lives. Hydrophilic polymers that can be excreted mostly unchanged through urine have shorter half-life than polymers that require some transformation before excretion. For example, since 24,000 DA is the cut-off for glomerular filtration, any polymer heavier than 24,000 DA needs to be degraded to some extent before it can be excreted, which extends the polymer's half-life. In some embodiments, the vessel closing compound has a half life less than 2 hours, and more preferably less than 1 hour. Such compounds may be selected from polymers with hydrophilic properties having a molecular weight less than 24,000 DA.

The vessel closing compound may be selected from a hydrophilic or an amphipathic polymer. The term "hydrophilic polymer," as used herein, means any macromolecule which exhibits an affinity for or attraction to water molecules and which comprises multiple instances of an identical subunit ("monomer") connected to each other in chained and/or branched structures. The hydrophilic polymer component may be a synthetic or naturally occurring hydrophilic polymer.

Naturally occurring hydrophilic agents include, but are not limited to, proteins such as collagen and derivatives thereof, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; methyl cellulose, sodium carboxylmethyl cellulose and activated polysaccharides such as dextran and starch derivatives.

Useful synthetic hydrophilic compounds include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), poly(polyethylene glycol methacrylate), poly(glycerol methacrylate), poly(glycerol acrylatete), poly(polyethylene glycol acrylate), poly(alkyl oxazoline), phosphoryl choline polymers, sodium and potassium polymethacrylate, sodium and potassium polyacrylate, polymethacrylatic acid and polyacrylic acid, propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly(ethyloxazoline); and polyvinylamines.

The term "amphipathic polymer" as used herein refers to any macromolecule which have localized quantum variations in charge giving rise to polar substructures and nonpolar substructures. The polar substructures evidence an affinity for or attraction to other polar molecular structures such as water molecules (hydrophilic), while the nonpolar substructures exhibit an affinity or attraction for nonpolar molecules such as lipids, oils, greases, fats, etc. (lipophilic). Suitable amphipathic polymers include, but are not limited to, poloxamer P-188, polyetherester copolymers such as polyethylene glycol and polylbutylene terephthalate copolymers, polyethylene glycol and polypropylencoxide copolymers, polyethylene glycol and polypropylene glycol block copolymers.

Amphipathic polymers also include a family of polyetheramines known as Jeffamine®. These polyetheramines contain primary amino groups attached to the end of a polyester backbone, which is typically based on propylene oxide (PO), ethylene oxide (EO), or a mixture thereof. The Jeffamine® family includes monamines, diamines, triamines and secondary amines. Jeffamine® may be procured from Huntsman Corporation, headquartered in The Woodlands, Tex.

In general, the concentration of the vessel closing compound in the instant compositions may range between about 0.1 and about 45% weight to volume, i.e. about 0.1 to about 45 gm of the vessel closing compound to 100 ml solution. In compositions for local administration, the concentration of the vessel closing compound is preferably between about 0.1 and about 20% weight to volume, and more preferably between about 1 to 10% weight per volume. In compositions prepared for parenteral administration, the concentration may be between about 10% and about 45% weight per volume or about 20 to about 40% weight to volume.

In some embodiments, the vessel closing agent may comprise polyethylene glycol. PEG of molecular weights between about 1000 and 24,000 DA, more preferably between about 1000 to 8000 DA are suitable, and most preferably between about 2,000 DA and about 4,000 DA for use as vessel closing compounds in instant compositions. PEGs of different molecular weights may be obtained from, for example, Sigma-Aldrich, St. Louis, Mo., USA.

In addition to the vessel closing compound, the instant compositions may include one or more active agents. The term "active agent," as used herein, refers to a chemical element or compound that has blood flow modifying activity and/or improves the effect of the vessel closing compound. In some embodiments, the active agent may alleviate signs or symptoms associated with a hemorrhagic condition. Suitable active agents may be selected from blood flow modifying agents, such as, for example, magnesium, potassium, nitric oxide, corticotropin-releasing hormone, parathyroid hormone, bradykinin molecules and derived fragments. The concentration of such active agents in the instant compositions may range between about 0.1% to about 20% weight per volume, and more preferably between 0.1 and 10% weight per volume.

In some embodiments, the instant compositions comprise a vessel closing compound and at least one active agent where the interaction between the vessel closing compound and the at least one active agent is mainly of an ionic nature. For example, although the hydrophilic polymer PEG as a whole is non-ionic, the lone pairs of the electrons on the ether oxygens on the PEG chains imparts an anionic character to the polymer and can bind to a metal ion with blood flow modifier activity such as magnesium In one embodiment, the active agent comprises a magnesium compound. Various magnesium salts may provide a source for the magnesium compounds. Suitable magnesium salts include, but are not limited to, magnesium sulfate, magnesium carbonate, magnesium chloride, magnesium oxide and magnesium hydroxide. These compounds are readily available commercially from, for example, Sigma Aldrich, St. Louis, Mo., USA.

Instant compositions may also include additional ingredients selected from such broad categories as, for example, disease-modifying agents, neurotransmitter, neuropeptides and neuronal receptor modulators, anti-inflammatory and immunomodulator agents, antioxidants, anti-apoptotic agents; nootropic and growth agents, modulators of lipid formation and transport, modulators of blood flow and vessel formation, analgesics, steroidal anti-inflammatory drugs such as corticosteroids, non-steroidal anti-inflammatory drugs such as salicylates, COX-2 inhibitors, TNFα inhibitors, opiates and morphinomimetics, among others.

In addition to the vessel closing compound and the active agents, the instant compositions may include one or more pharmaceutically acceptable carriers. The instant compositions may include excipients such as solvents, binders, fillers, disintegrants, lubricants, suspending agents, surfactants, viscosity increasing agents, buffering agents, antimicrobial agents, among others. Many different pharmaceutically acceptable carriers and excipients are known and disclosed, for example, in Remington's Pharmaceutical Sciences, Lippincott Williams & Wilkins; 21 edition (May 1, 2005).

By way of non-limiting examples, compositions disclosed in U.S. patent application Ser. Nos. 11/418,153 and 11/418,152, incorporated herein by reference in their entireties, may be employed.

In some embodiments, the instant compositions may be prepared as liquid solutions, solid forms suitable for solution in liquid prior to injection. The instant compositions may be administered parenterally, preferably by intravenous administration. It was found that intravenous administration may lead to a higher accumulation of the vessel closing agent at the site of hemorrhage relative to other modes of administration, such as intraperitoneal injection because intravenous administration provides a more direct and, thus, faster access to systemic circulation. Alternatively, the instant compositions may be delivered locally to the site of the vessel rupture and in some instance delivery could be assisted by a device such as a pump or pulsative device.

As noted above, the compounds that are preferred for use as vessel closing compounds accumulate at the site of hemorrhage and are rapidly cleared from the rest of the system. Because such polymers are likely to have a short half life in the body, they need to be administered to a patient rapidly. More specifically, it is desirable to administer a dose of the instant composition to the patient within one half-life or less of the vessel closing compound. For example, the half-life of PEGs having a molecular weight between 1000 and 6000 Da is about 30 to 90 minutes, and thus it is desirable to administer a dose of the instant composition comprising such PEGs within 90 minutes, and more preferably within 60 minutes.

Having now generally described the invention, the same may be more readily understood through the following reference to the following example, which is provided by way of illustration and is not intended to limit the present invention unless specified.

EXAMPLE

Methods and Tests

Male Sprague-Dawley Rats were anesthetized and placed in a prone position on a stereotaxic frame. A T9/10 laminectomy was performed and animals were contused at a displacement of 1.5 mm with the Ohio State University impactor.

Soon after injury, saline, 0.8% magnesium in saline, 0.8% magnesium in 20% or 30% PEG3350, PEG-biotin or magnesium in a PEG3000-biotin formulations were administered by intravenous infusion of 5-7 mL/kg over a 10-30-min period. Animals received 1 to 5 infusions with an interval of 6 hours between infusions. The contents of the infusion vials were blinded to the investigators performing both the infusions and the analyses.

Figure 3B:
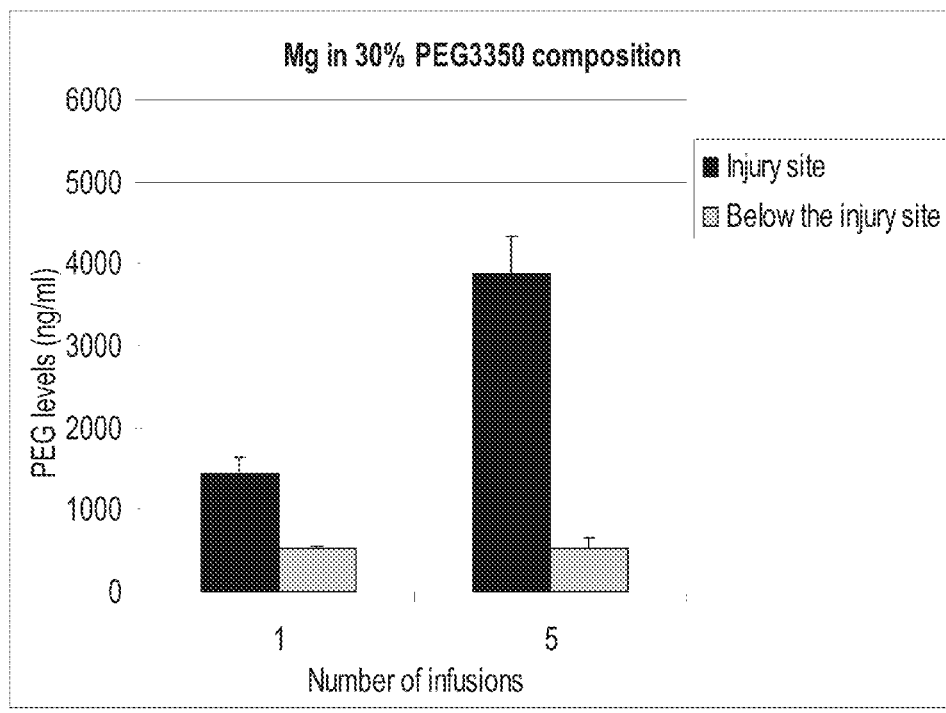
Figure 4:
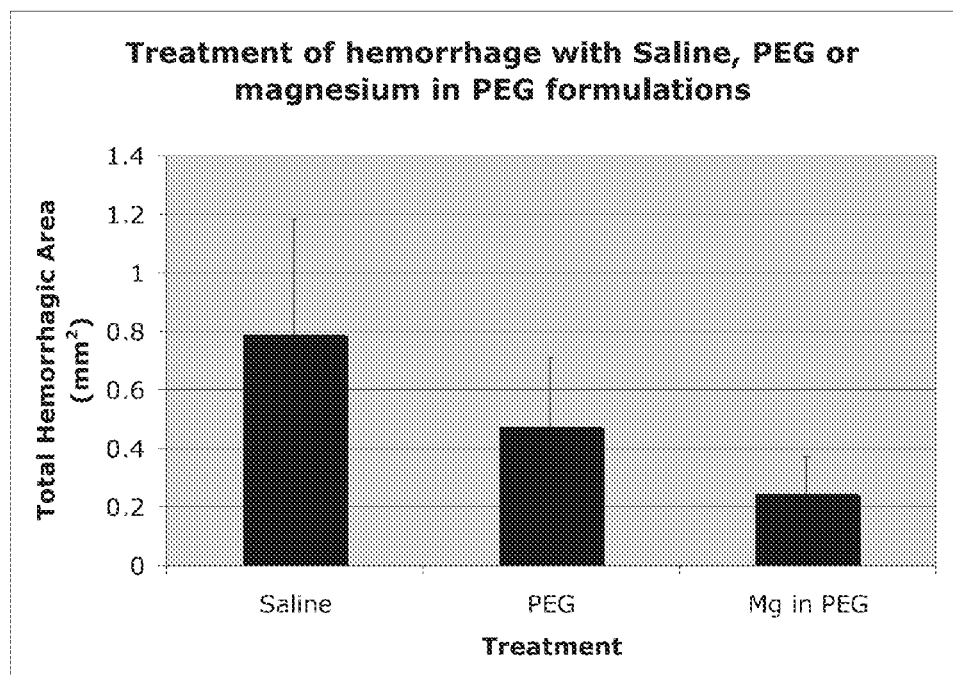
FIG. 4 presents data showing the extent of the hemorrhagic area following administration of saline, PEG or Magnesium in PEG solution.

At various time points after infusion, the tissue we extracted and processed for histological evaluation (FIGS. 1-2), bioanalytical analysis (FIG. 3) or functional analysis (FIG. 4).

For the histology analysis presented at FIGS. 1 and 2, the cords were harvested at the indicated timepoints, cut horizontally at 20 um thickness and processed using the colorimetric ABC kit that includes reaction with avidin-peroxidase complexes and the peroxidase susbrate DAB leading to the development of a brown color where the biotin molecules (here the PEG-biotin) are located.

For the bioanalytical analysis presented at FIG. 3, tissue containing or not the site of hemorrhage were collected. Tissue concentrations of PEG in rat plasma were measured using a validated high performance liquid chromatograpy tandem mass spectrometry (HPLC/MS/MS) method in positive electrospray ionization mode. Following centrifugation of the tissue homogenate, the supernatant fraction from each sample was concentrated by evaporation and reconstituted with mobile phase A prior to analysis. The samples were analyzed with an HPLC/MS/MS assay using a Thermo Hypersil ODS column. The peak areas of PEG and the theoretical concentrations of calibration standards were fit to the ln-quadratic function, excluding the origin.

The following method describes the functional analysis or evaluation of the extent of hemorrhage at the injury site. At 72 hours post-injury, the animals were decapitated and a 15 mm segment of the spinal cord centered around the hemorrhagic site was collected and frozen and cyrosectioned at a thickness of 20 um. Eleven sections per cord were selected for analysis: the epicentre of injury, and the sections rostral and caudal 400 um, 800 um, 1600 um, 2800 um, and 3200 um. The slides were cover slipped and color images of the spinal cords were obtained at 5× objective using a Leica light microscope. The red channel (representing bleeding into the tissue) was captured on a greyscale image, and the intensity threshold was set at 230 across all images to remain consistent throughout. The spinal cords, excluding the dura and blood trapped underneath, were circled in green. The overlapping signals of expressed red and circled green was highlighted with blue using the Overlay Math function under Image from the toolbar in Sigma Scan and the total area of blue signal was measured as the extent of hemorrhage.

Results:

(1) PEG accumulates and is retained preferentially at the hemorrhagic site following a single parenteral administration.

Referring to FIG. 1, histological DAB staining following parenteral administration of the biotin-labeled PEG solution indicated that the biotin-labeled PEG accumulates preferentially at the hemorrhagic site with no visible accumulation in the spinal cord regions above or below the site of injury. PEG could be detected at the hemorrhagic site within 2 hours after administration (FIG. 1a), the PEG signal increased over 24 hours after administration (FIG. 1b) and had largely disappeared by 7 days post-administration (FIG. 1c). Non-specific DAB staining was absent in the spinal cords of saline-treated animals (FIGS. 1d-f).

(2) PEG accumulation at the hemorrhagic site is influenced by the mode of administration Referring to FIG. 2, histological DAB staining indicated that significantly higher accumulation and retention of the biotin-labeled PEG was achieved 24 hours following a single intravenous injection (FIGS. 2e-f) relative to a single intraperitoneal injection (FIGS. 2b-c) of the biotin-labeled PEG solution. However, there was no obvious difference in the biotin-labeled PEG signal found at the hemorrhagic site 2 hours following intravenous injection or intraperitoneal injection of the biotin-labeled PEG solution (FIGS. 2a and 2d).

(3) Compositions of 20% and 30% of PEG solution lead to similar accumulations of PEG at the hemorrhagic site after a single or repeated intravenous infusions.

Quantitative evaluation of PEG spinal tissue levels using HPLC/MS/MS assay indicated that PEG accumulates preferentially at the hemorrhagic site following one intravenous infusions of a magnesium in 20% PEG3350 solution with PEG tissue levels of 936 ng/ml found at the hemorrhagic site relative to 315 ng/ml at a non-injured site at 3 hours post-infusion. Following five infusions of magnesium in 20% PEG3350 solution with an interval of 6 hours between each infusion, the PEG tissue levels reached 4025 ng/ml at the hemorrhagic site relative to 595 ng/ml at a non-injured site 3 hours after the last infusion. Similarly, following a single intravenous administration of magnesium in 30% PEG3350 solution, PEG tissue levels of 1430 ng/ml were found at the hemorrhagic site relative to 519 ng/ml at a non-injured site at 3 hours post-infusion. Following five infusions of magnesium in 30% PEG3350 solution with an interval of 6 hours between each infusion, the PEG tissue levels reached 3891 ng/ml at the hemorrhagic site relative to 526 ng/ml at a non-injured site 3 hours after the last infusion.

Intravenous administration of PEG reduces the extent of the hemorrhage at the site of injury. Addition of magnesium to the PEG formulation further decreases the hemorrhagic signal.

Quantitative morphometric analysis of the hemorrhagic signal within an area covering 3.2 $mm^2$ of the epicenter of the injury site. Saline treatment following SCI in rats led to bleeding detected in an area size of 0.79 $mm^2$. The extent of the bleeding area was reduced to 0.47 $mm^2$ following intravenous administration of a PEG solution and further reduced to 0.25 $mm^2$ following intravenous administration of a magnesium in PEG solution.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention which is defined by the following claims.

What is claimed is:

1. A method of reducing the size of a hemorrhage comprising:
   diagnosing one or more hemorrhaging vessels in a patient; and
   administering intravenously or locally to the patient an injectable formulation comprising magnesium having a concentration of about 0.8% weight per volume and about 20% weight per volume of polyethylene glycol (PEG), wherein the PEG has a molecular weight between about 2,000 and about 4,000 Da.

2. The method of claim 1, wherein hemorrhaging is induced by a mechanical, an electrical, a biological, or a chemical injury.

3. The method of claim 1, wherein the formulation can modify blood flow.

4. The method of claim 3, wherein the magnesium can form an ionic bond with the PEG.

5. The method of claim 1, wherein the formulation is administered at least one time at a dosing rate of at least about 0.1 to about 10 ml/kg.

6. The method of claim 1, wherein the formulation is administered locally using a pulsative device.

7. The method of claim 1, wherein the PEG comprises a molecular weight of 3350 Da.

8. The method of claim 1, wherein the formulation comprises an antioxidant.

9. The method of claim 1, wherein the magnesium comprises magnesium sulfate, magnesium carbonate, magnesium chloride, magnesium oxide or magnesium hydroxide.

10. The method of claim 1, wherein the formulation is administered by intravenous infusion.

11. The method of claim 1, wherein the PEG comprises about 20% weight per volume of PEG3350.

12. The method of claim 1, wherein the method reduces the size of a spinal cord hemorrhage.

13. A method of reducing the size of a hemorrhage comprising:
   diagnosing one or more hemorrhaging vessels in a patient; and
   administering intravenously or locally to the patient an injectable formulation comprising magnesium having a concentration of about 0.8% weight per volume and about 30% weight per volume of polyethylene glycol (PEG), wherein the PEG has a molecular weight between about 2,000 and about 4,000 Da.

14. The method of claim 13, wherein the PEG comprises about 30% weight per volume of PEG3350.

* * * * *